United States Patent
Shimoe et al.

(10) Patent No.: US 6,867,345 B2
(45) Date of Patent: Mar. 15, 2005

(54) DISPOSABLE BODY FLUID ABSORBENT ARTICLE HAVING LONGITUDINAL SIDE GROOVE

(75) Inventors: Nariaki Shimoe, Kagawa-ken (JP); Yoshinori Kumasaka, Kagawa-ken (JP); Yasushi Inoue, Kagawa-ken (JP); Toshifumi Otsubo, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/458,077

(22) Filed: Dec. 10, 1999

(65) Prior Publication Data

US 2003/0187416 A1 Oct. 2, 2003

(30) Foreign Application Priority Data

Dec. 11, 1998 (JP) ............................................. 10-353396

(51) Int. Cl.[7] ............................ A61F 13/15; A61F 13/20
(52) U.S. Cl. .................................. 604/378; 604/385.01
(58) Field of Search ................................ 604/379–383, 604/385.01, 358

(56) References Cited

U.S. PATENT DOCUMENTS

| | | | | |
|---|---|---|---|---|
| 3,749,627 A | * | 7/1973 | Jones ........................... | 156/268 |
| 3,929,135 A | * | 12/1975 | Thompson ................ | 604/385.08 |
| 4,059,114 A | * | 11/1977 | Richards ...................... | 128/287 |
| 4,758,240 A | * | 7/1988 | Glassman ................... | 604/379 |
| 4,790,838 A | * | 12/1988 | Pigneul et al. .............. | 604/366 |
| 5,092,860 A | * | 3/1992 | Pigneul ........................ | 604/380 |
| 5,308,346 A | * | 5/1994 | Sneller et al. ............ | 604/385.2 |
| 5,397,316 A | * | 3/1995 | LaVon et al. ................ | 604/369 |
| 5,451,442 A | | 9/1995 | Pieniak et al. | |
| 5,817,271 A | * | 10/1998 | Congleton et al. .......... | 264/400 |
| 5,833,679 A | | 11/1998 | Wada | |
| 5,891,118 A | * | 4/1999 | Toyoshima et al. ......... | 604/366 |
| 5,891,121 A | * | 4/1999 | Redwine et al. ............ | 604/387 |
| 6,139,912 A | * | 10/2000 | Onuschak et al. .......... | 427/180 |
| 6,176,954 B1 | * | 1/2001 | Tsuji et al. .................. | 156/178 |
| 6,306,123 B1 | * | 10/2001 | Salerno et al. ......... | 604/385.31 |

FOREIGN PATENT DOCUMENTS

| | | |
|---|---|---|
| DE | 196 35 718 | 3/1997 |
| EP | 0 758 543 | 2/1997 |
| EP | 0 769 284 | 5/1997 |
| JP | 1-141707 | 9/1989 |
| JP | 2-84623 | 7/1990 |
| JP | 5-39691 | 10/1993 |
| JP | 9-51913 | 2/1997 |
| JP | 9-108262 | 4/1997 |

* cited by examiner

*Primary Examiner*—Larry I. Schwartz
*Assistant Examiner*—Michele Kidwell
(74) *Attorney, Agent, or Firm*—Lowe Hauptman & Berner, LLP

(57) ABSTRACT

A disposable body fluid absorbent article includes a liquid-absorbent core. The core is provided in the vicinity of opposite side edges extending in a longitudinal direction with depressed regions tapering from an upper surface toward a lower surface of the core. A density of the core components in the depressed regions is lower then or equal to a density of the core components in the remaining region of the core.

21 Claims, 5 Drawing Sheets

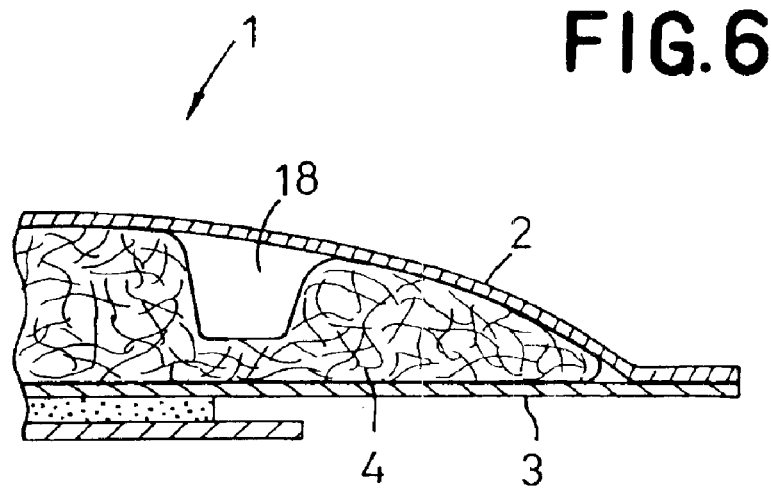
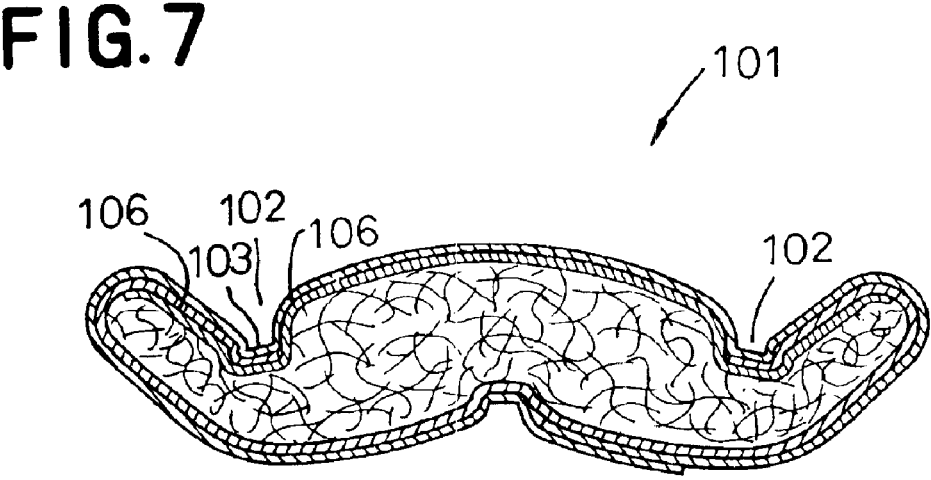

DISPOSABLE BODY FLUID ABSORBENT ARTICLE HAVING LONGITUDINAL SIDE GROOVE

FIELD OF THE INVENTION

The present invention relates to a disposable body fluid absorbent article such as a disposable diaper, a sanitary napkin or the like.

BACKGROUND OF THE INVENTION

Japanese Utility Model Application Disclosure Gazette (Kokai) No. Hei1-141707, Japanese Utility Model Application Disclosure Gazette (Kokai) No. Hei2-84623 and Japanese Patent Application Disclosure Gazette (Kokai) No. Hei9-51913 disclose a disposable diaper including grooves extending through a thickness of a liquid-absorbent core or grooves dividing the liquid-absorbent core in a plurality of sections in the transverse direction of the absorbent core. Along these grooves, a topsheet and a backsheet of the diaper are bonded to each other to define bottoms of the respective grooves.

Japanese Utility Model Application Publication (Kokoku) No. Hei5-39691 and Japanese Patent Application Disclosure Gazette (Kokai) No. Hei9-108262 disclose a sanitary napkin having a liquid-absorbent core compressed in the direction from a topsheet toward a backsheet or in the reverse direction to form grooves extending in the longitudinal direction of the napkin. The liquid-absorbent core presents a remarkably high density along bottoms of the grooves.

In the prior art article described above, when the topsheet and the backsheet are bonded to each other to define the bottoms of the respective grooves, an amount of body fluids that has flown into the grooves might stay and gives a wearer of the article, such as a diaper, a feeling of wetness causing the wearer's discomfort. The reason is that the liquid-absorbent core of a disposable diaper or a sanitary napkin generally has a limited thickness and the side walls of the grooves are correspondingly limited in a total surface area even if the grooves are intended to absorb the amount of body fluids flowing therein.

FIG. 7 is a sectional view showing a transverse cross-section of a napkin 101 described in the Japanese Utility Model Application Publication Gazette (Rokoku) No. Hei5-39691. The napkin 101 solves the above problem, i.e., prevents body fluids from staying in grooves 102 by placing portions of a liquid-absorbent core 104 under bottoms 103 of the respective grooves 102. However, the portions of the liquid-absorbent core 104 immediately underlying the bottoms 103 have been compressed to have relatively high density and rigidity of the core 104 is correspondingly high in these portions. To alleviate an adverse effect of the relatively high density, opposite side walls 106 of the respective grooves 102 are tapered toward the bottoms 103 to define a U- or V-shaped section of the liquid-absorbent core 104 in the vicinity of each groove 102.

The napkin 101 of FIG. 7 formed on both side regions with such grooves 102 can not smoothly placed against a crotch region of the wearer with the napkin 101 being curved over its full width substantially in an inverted U-shape. In an inverted embodiment of the napkin 101 of FIG. 7, the napkin may be formed on its both side regions with grooves by compressing the napkin from the backsheet toward the topsheet to facilitate the napkin to crook or curve over its full width substantially in an inverted U-shape. However, there is still an apprehension that the bottoms of the respective inverted grooves, having a relatively high rigidity, might directly stimulate soft skin in the wearer's crotch region. In addition, it is impossible for such a napkin to offer the desired function and effect of preventing body fluids from leaking sideways by receiving and absorbing an amount of the body fluids, flowing on the topsheet transversely of the napkin, in the grooves.

SUMMARY OF THE INVENTION

In view of the above problems, it is a principal object of this invention to provide an improved disposable article, such as a sanitary napkin, which is easy to curve over its fill width with the topsheet facing a crotch region of a wearer without stimulating the wearer's skin.

According to the present invention, there is provided a disposable body fluid absorbent article adapted to be placed against a crotch region of a wearer to absorb body fluids, comprising a liquid-absorbent core having an upper surface covered with a liquid-pervious topsheet and a lower surface, and the liquid-absorbent core being provided in the vicinity of opposite side edges extending in a longitudinal direction thereof with depressed regions tapering from the upper surface toward the lower surface and along a pair of imaginary lines extending in the longitudinal direction so as to describe convex curves respectively facing a center line bisecting a width of the liquid-absorbent core.

According to one embodiment of the present invention, the depressed regions continuously extend along the imaginary lines.

According to another embodiment of the present invention, the depressed regions intermittently extend along the imaginary lines.

According to still another embodiment of the present invention, the liquid-absorbent core contains a fibrous component and a density of the fibrous component in the depressed regions is equal to or lower than a density of the fibrous component in the remaining region.

According to further another embodiment of the present invention, the liquid-absorbent core further contains super-absorptive polymer particles distributed only in a region defined inside the imaginary lines about the center line.

DESCRIPTION OF THE DRAWINGS

FIG. 6 is a view similar to FIG. 2 showing a sanitary napkin according to still another ment of the present invention; and FIG. 7 illustrates a typical prior art napkin in its transverse section.

DETAILED DESCRIPTION OF THE PREFERRED-EMBODIMENTS

Details of a disposable body fluid absorbent article according to the present invention will be more fully understood from the description given hereunder with reference to the accompanying drawings which illustrate specific embodiments of the sanitary napkin of the present invention.

Figure 1:
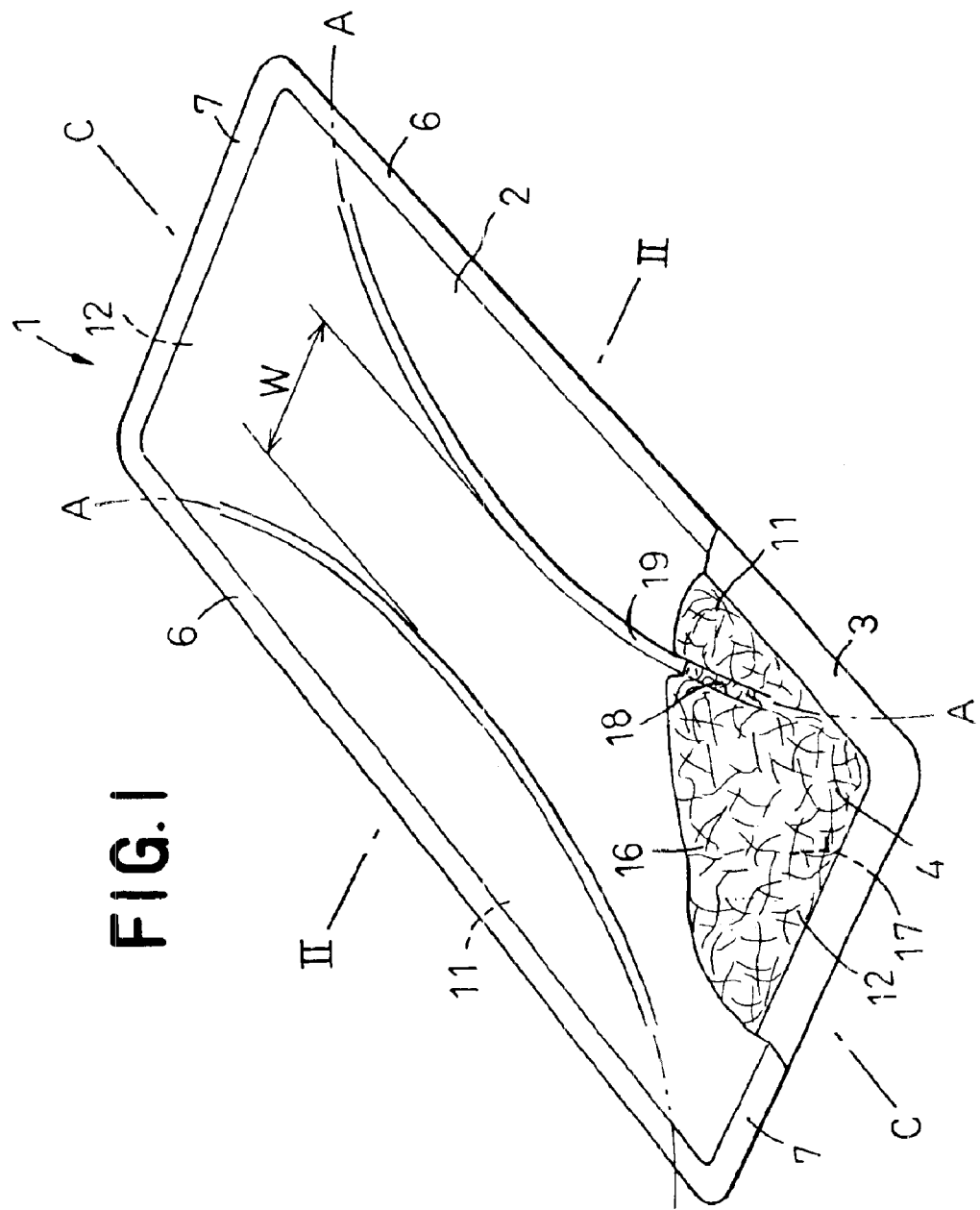
FIG. 1 is a perspective partially exploded view, showing a sanitary napkin constructed ng to the present invention.

A sanitary napkin 1 shown in FIG. 1 comprises a liquid-pervious topsheet 2, a liquid-impervious backsheet 3 and a liquid-absorbent core 4 disposed between the topsheet 2 and the backsheet 3. The topsheet 2 and the backsheet 3 extend outward beyond a peripheral edge of the liquid-absorbent core 4 and are put flat and bonded together along the extension.

The napkin 1 is substantially configured as a narrow rectangle defined by opposite side edges 6 extending in a longitudinal direction and opposite ends 7 extending in a transverse direction. The liquid-absorbent core 4 is also configured as a narrow rectangle defined by opposite side regions 11 and opposite end regions 12. The core 4 has an upper surface 16 covered with the topsheet 2 and a lower surface 17 covered with the backsheet 3. The upper surface 16 is formed with a pair of first grooves 18 extending along a pair of imaginary lines, for example, lines A—A as seen in FIG. 1, describing convex curves respectively facing a center line C—C bisecting a width of the napkin 1. The topsheet 2 is formed with a pair of second grooves 19 depressed and curved in coincidence with the first grooves 18. The minimum dimension W by which the pair of first grooves 18 are spaced from each other transversely of the napkin 1 is preferably in a range of 20–40 mm.

Figure 2:
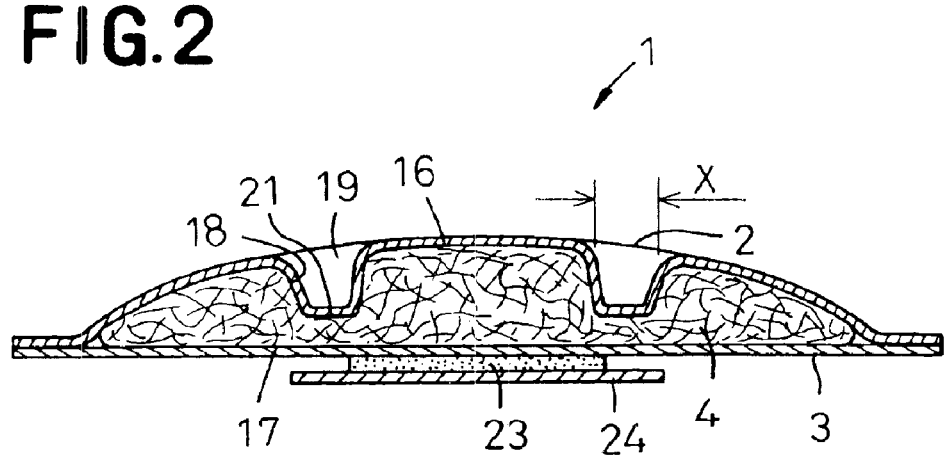
FIG. 2 is a sectional view taken along a line II—II in FIG. 1.

FIG. 2 is a sectional view taken along a line II—II bisecting a length of the napkin 1. The liquid-absorbent core 4 may have a thickness gradually decreasing from a transversely middle region toward the opposite side edges of the napkin 1, or a substantially uniform thickness except the regions defined by bottoms 21 of the first grooves 18 in which the thickness of the core 4 is abruptly decreased. Specifically, the thickness of the core 4 is approximately 1–15 mm in the transversely middle region and 10–80% thereof in the regions defined by the bottoms 21. Each of the first grooves 18 has a width X of approximately 1–10 mm at its open top from which the first groove 18 is tapered toward its bottom 21. A depth of the first groove 18 gradually decreases from its longitudinally middle region toward its longitudinally opposite ends until the groove 18 disappears.

The liquid-absorbent core 4 comprises hydrophilic fibers such as fluff pulp or hydrophobic fibers treated to become hydrophilic of 100–40% by weight, superabsorptive polymer particles of 0–60 by weight and hydrophobic fibers of 0–20% by weight. The core 4 has a remarkably low rigidity at the respective bottoms 21 of the first grooves 18 due to particular thickness and composition in these regions. A fiber density in the regions defined by the bottoms 21 is equal to or lower than that in the remaining region and an amount of the polymer particles in the regions defined by the bottoms 21 is equal to or less than that in the remaining region. More preferably, the polymer particles are distributed only in the region extending from the respective imaginary lines A—A to the center line C—C of then core 4 and not distributed in the regions defined by the bottoms 21. By distributing the polymer particles in this manner, it is possible to avoid an apprehension that the polymer particles might absorb a partial amount of body fluids and consequently form gel blocks. Such gel blocks might obstruct a smooth movement of the body fluids in the transverse direction of the core 4. It is not apprehended that the first grooves 18 might be filled up with polymer particles swollen by absorption of the body fluids.

The topsheet 2 is made of a liquid-pervious nonwoven fabric or a porous plastic film and may be intermittently bonded to the upper surface 16 of the core 4, if desired. The backsheet 3 is made of a liquid-impervious plastic film and may be intermittently bonded to the lower surface 17 of the core 4, if desired. The backsheet 3 is applied on its lower surface with adhesive 23 by which the napkin 1 is attached to an undergarment worn by a wearer and the adhesive 23 is covered with a release paper 24.

Figure 3:
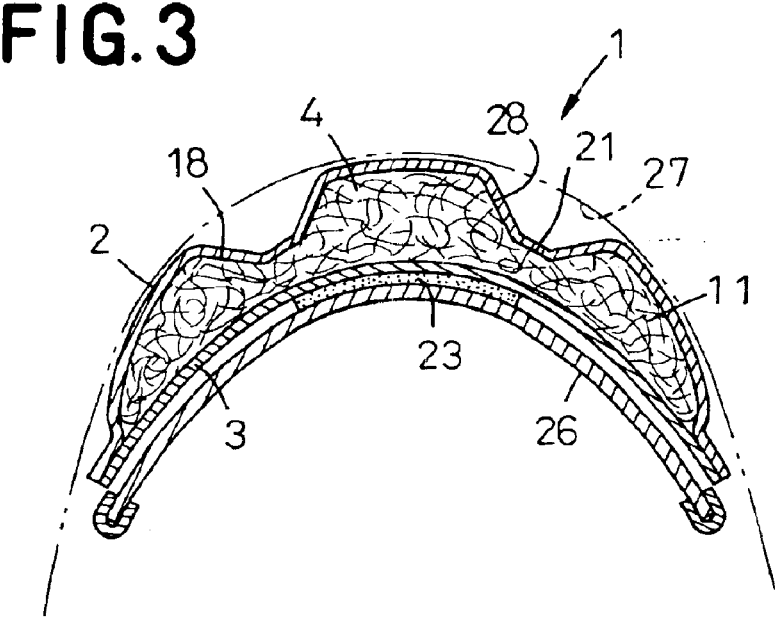
FIG. 3 is a view similar to FIG. 2 showing the sanitary napkin as it is put on a wearer's body.

FIG. 3 is a view similar to FIG. 2 showing the napkin 1 as put on the wearer's body. The napkin 1 is attached by means of the adhesive 23 to the inner surface of the undergarment 26 on a crotch region thereof and placed against a crotch region 27 of the wearer. As seen in FIG. 3, the napkin 1 is put on the wearer's body so that the napkin 1 describes an inverted U-shape with the topsheet 2 defining the outer side thereof. With the napkin 1 according to the present invention, the opposite side regions 11 of the core 4 easily crook or curve downward along the first grooves 18 having a relatively low density and thereby ensuring a good fit to the wearer's crotch region without giving the wearer any feeling of incompatibility. Along the first grooves 18, an amount of body fluid flowing thereinto can be absorbed by the core 4 through the topsheet 2 on opposite side walls 28 as well as on the bottoms 21 of the first grooves 18.

Figure 4:
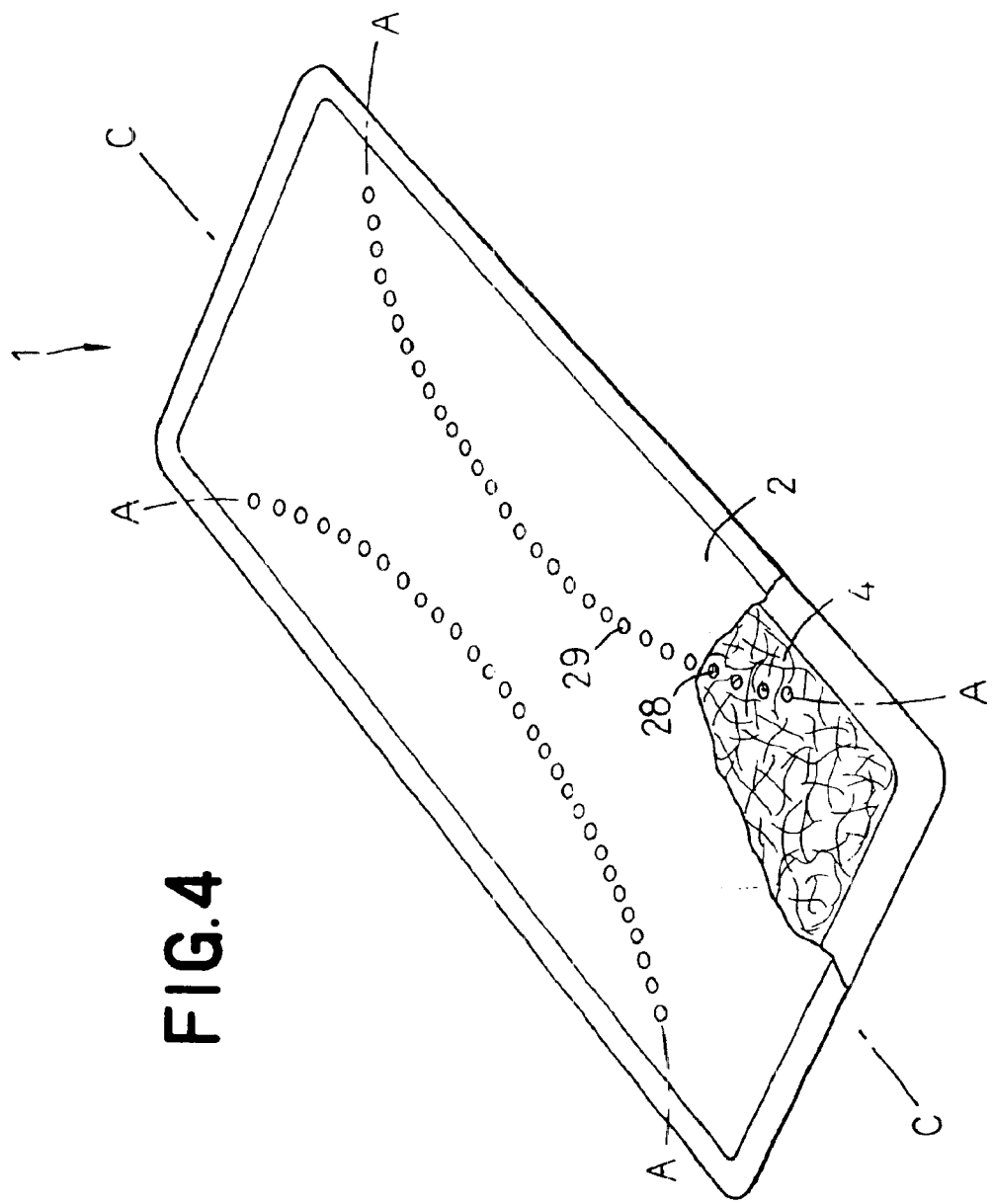
FIG. 4 is a view similar to FIG. 1 showing a sanitary napkin according to one ment of the present invention.

FIG. 4 is a view similar to FIG. 1 showing one embodiment of the present invention. According to the embodiment, the core 4 of the napkin 1 is formed with a plurality of first depressions 28 intermittently arranged along the pair of imaginary lines A—A and the topsheet 2 is formed with a plurality of second depressions 29 arranged in close contact with the first depressions 28, respectively. The first and second depressions 28, 29 replace the first and second grooves 18, 19 in FIG. 1. The individual depressions are shaped to be circular or oval. Each of the first depressions 28 has a dimension substantially corresponding to the dimension of the first groove 18 as measured transversely of the napkin 1 and has a depth which is also substantially corresponding to the depth of the first groove 18.

Figure 5:
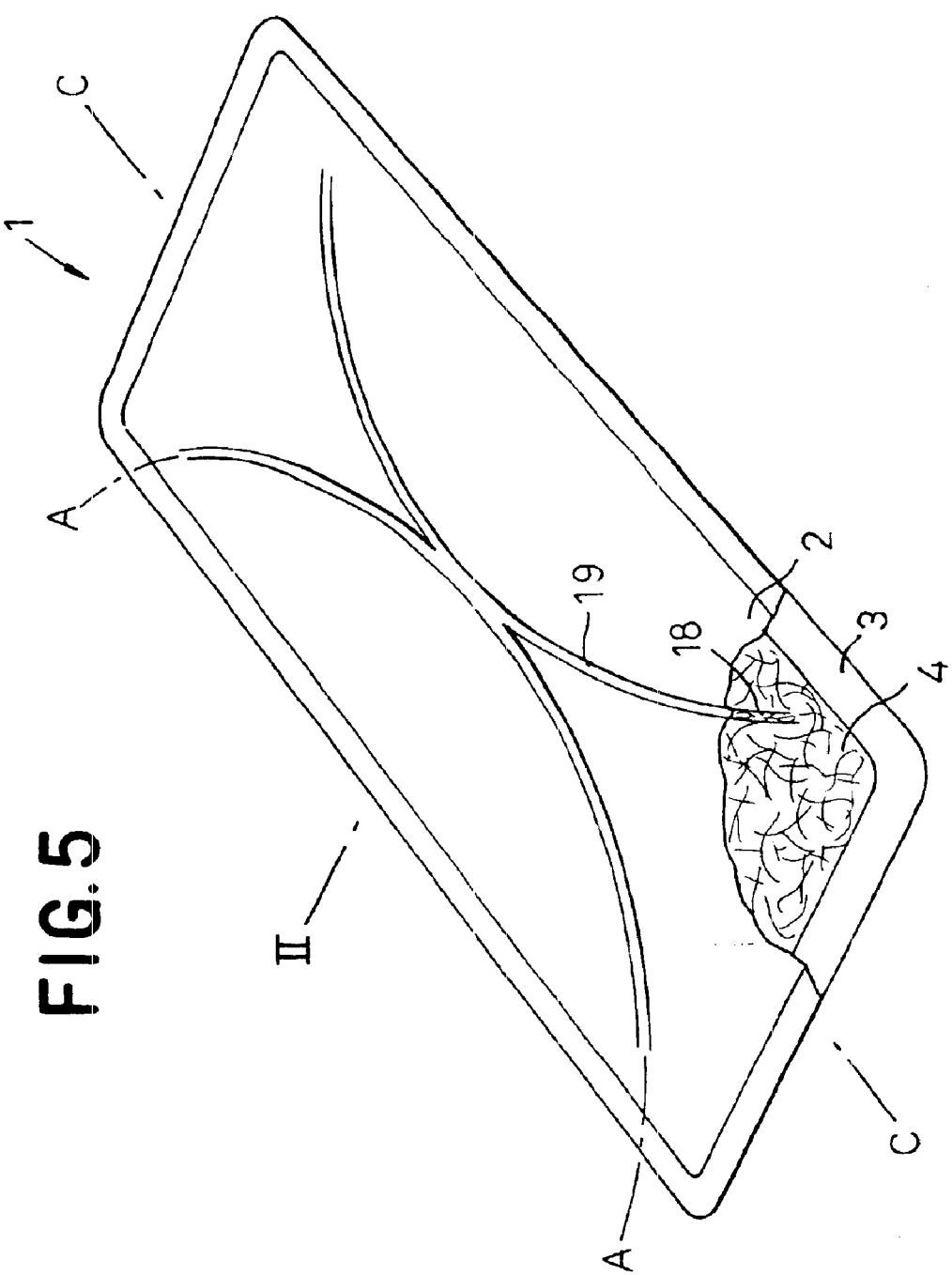
FIG. 5. is a view similar to FIG. 1 showing a sanitary napkin according to another ment of the present invention.

FIG. 5 is a view similar to FIG. 1 showing a napkin according to another embodiment of the present invention. Similarly to FIG. 1, the napkin 1 according to this embodiment has a pair of first grooves 18 and the corresponding pair of second grooves 19 extending transversely of the napkin 1. This embodiment differs from FIG. 1 in that the grooves 18, 19 formed on both sides of the napkin 1 come in contact on the center line C—C so that the grooves 18, 19 on both sides describe together a curved X-shape. In other words, the first and second grooves 18, 19 extend transversely of the napkin 1 along a pair of imaginary curves A—A which are convex toward the center line C—C.

FIG. 6 is a view similar to FIG. 2 showing a napkin 1 according to still another embodiment of the present invention. The napkin 1 differs from the precedent embodiments in that the topsheet 2 is not formed with the pair of second grooves 19 to be aligned with the pair of first grooves 18 formed, also in the case of the napkin 1, on the core 4 and merely covers the respective open tops of the first grooves 18. The napkin 1 according to the embodiment also is easily deformable in the inverted U-shape as the napkin 1 is put on the wearer's body. However, it is apprehended that the napkin 1 might be less reliable than the napkin 1 of FIG. 1 in its function and effect to prevent the partial amount of menstrual discharge flowing on the topsheet 2 transversely of the napkin 1 from leaking sideways by receiving such amount of menstrual discharge-in the pair of second grooves 19 and absorbing this through the bottoms as well as through the opposite side walls of the second grooves 19.

While the present invention-has been described hereinabove by way of example in the form of sanitary napkin 1, it should be understood that the present invention is not limited to the sanitary napkin and applicable also to the other various disposable garments such as disposable diaper and disposable undergarment particularly for persons suffering from incontinence.

The disposable body fluids absorbent article according to the present invention is provided on both sides of the liquid-absorbent core with the depressions tapering from the upper surface toward the lower surface of the liquid absorbent core so that the body fluids may be absorbed through the bottoms as well as through the opposite side walls of these depressions. This unique arrangement is effective to avoid an apprehension that the body fluids might stay in these depressions and give the garment wearer undesirable feeling of high wetness and discomfort due to such feeling of high wetness. Furthermore, a rigidity of the liquid-absorbent core is remarkably lower along the bottoms of the respective depressions than in the vicinity thereof. Such unique distribution of the rigidity facilitates the liquid-absorbent core to crook or curve along the depressions over a full width of the core substantially in the inverted U-shape as the napkin is put on the wearer's body.

What is claimed is:

1. An absorbent article, comprising:

a liquid-permeable topsheet; and a liquid-absorbent core having an upper surface covered by said topsheet and a lower surface, said core further having indented regions arranged along two lines extending longitudinally along transversely opposite sides of said core, said lines being spaced apart from each other by a distance gradually increasing from a minimum at a longitudinally middle point thereof to a maximum at longitudinally opposite ends thereof, the lines longitudinally dividing said core into a central region confined between the lines and two side regions each located between one of the lines and the respective one of the transversely opposite sides of said core;

wherein said core comprises a plurality of indentations arranged along said lines, each of said indentations having side walls extending from an opening formed on the upper surface toward the lower surface and ending at a bottom, a portion of said core confined between said bottom and said lower surface defining one of the indented regions; and said core contains a fibrous component in said indented, central and side regions, and a density of the fibrous component in the indented regions is lower than in the central and side regions.

2. The article of claim 1, wherein the indented regions continuously extend along said lines.

3. The article of claim 1, wherein said core further contains super-absorptive polymer particles, said indented regions are devoid of said super-absorptive polymer particles.

4. The article of claim 1, wherein a distance between the side walls decreases from the opening toward the bottom.

5. The article of claim 1, wherein the openings of the indentations arranged successively along each of said lines are contiguous so that to form at least two grooves each extending along one of said lines.

6. The article of claim 5, wherein each of the grooves extends for substantially an entire length of the respective line.

7. The article of claim 6, wherein the grooves intersect in a vicinity of the longitudinally middle point of said lines.

8. The article of claim 1, wherein said topsheet includes a plurality of portions each being received within a space defined by the side walls and bottom of one of the indentations, wherein said portion of said topsheet extends continuously within said space and includes at least a first section extending from the opening toward the bottom along one of the side walls, a second section extending from the bottom toward the opening along the other side wall, and a third section located between, contiguous to and connecting the first and second sections.

9. The article of claim 1, wherein said topsheet spans over the openings of the indentations without being partially received within spaces defined by the side walls and bottoms of the indentations.

10. The article of claim 1, wherein said lines intersect in a vicinity of the longitudinally middle point thereof.

11. The article of claim 1, wherein at least one of the side regions of said core has a thickness gradually decreasing from the respective one of the indented regions toward the respective one of the transversely opposite sides of said core.

12. The article of claim 1, wherein the central and side regions of said core have substantially the same thickness.

13. The article of claim 1, further comprising a liquid-impermeable backsheet covering the lower surface of said core and bonded to said topsheet.

14. The article of claim 1, wherein an entirety of said core is made of a fibrous material defining said fibrous component.

15. The article of claim 1, wherein a minimum thickness of said core in said central region is not lower than a maximum thickness of said core in the indented regions and side regions.

16. An absorbent article, comprising:

a liquid-permeable topsheet; and a liquid-absorbent core having an upper surface covered by said topsheet and a lower surface, said core further having indented regions arranged along two lines extending longitudinally along transversely opposite sides of said core, said lines being spaced apart from each other by a distance gradually increasing from a minimum at a longitudinally middle point thereof to a maximum at longitudinally opposite ends thereof, the lines longitudinally dividing said core into a central region confined between the lines and two side regions each located between one of the lines and the respective one of the transversely opposite sides of said core;

wherein said core contains a fibrous component and a non-zero density of the fibrous component in the indented regions is lower than in the central and side regions; and a plurality of said indented regions are arranged at intervals along each of said lines.

17. The article of claim 16, wherein said core comprises a plurality of indentations arranged along each of said lines, each of said indentations having side walls extending from an opening formed on the upper surface toward the lower surface and ending at a bottom, a portion of said core confined between said bottom and said lower surface defining one of the indented regions; and for each of said lines, the openings of the indentations arranged along said line are spaced from each other.

18. The article of claim 16, wherein an entirety of said core is made of a fibrous material defining said fibrous component.

19. The article of claim 16, wherein said core further contains super-absorptive polymer particles, said indented regions are devoid of said super-absorptive polymer particles.

20. An absorbent article, comprising:

a liquid-permeable topsheet; and a liquid-absorbent core having an upper surface covered by said topsheet and a lower surface, said core further having indented regions arranged along two lines extending longitudinally along transversely opposite sides of said core, said lines being spaced apart from each other by a distance gradually increasing from a minimum at a longitudinally middle point thereof to a maximum at longitudinally opposite ends thereof, the lines longitudinally dividing said core into a central region confined between the lines and two side regions each located between one of the lines and the respective one of the transversely opposite sides of said core;

wherein said core comprises a plurality of indentations arranged alone said lines, each of said indentations having side walls extending from an opening formed on the upper surface toward the lower surface and ending at a bottom, a portion of said core confined between said bottom and said lower surface defining one of the indented regions;

said core contains a fibrous component and a density of the fibrous component in the indented regions is lower than in the central and side regions;

the openings of the indentations arranged successively alone each of said lines are contiguous so that to form at least two groves each extending along one of said lines; and a depth of at least one of the grooves gradually decreases from the longitudinally middle point of the respective line toward the longitudinally opposite ends thereof.

21. The article of claim 20, wherein said core contains the fibrous component in said indented, central and side regions.

* * * * *